US00PP19385P3

(12) United States Plant Patent
Kordes

(10) Patent No.: US PP19,385 P3
(45) Date of Patent: Oct. 28, 2008

(54) HYBRID TEA ROSE PLANT NAMED 'KORTIGLO'

(50) Latin Name: *Rosa hybrida*
Varietal Denomination: KORtiglo

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/008,682

(22) Filed: Jan. 11, 2008

(65) Prior Publication Data

US 2008/0141401 P1 Jun. 12, 2008

(51) Int. Cl.
*A01H 5/00* (2006.01)

(52) U.S. Cl. ..... Plt./134

(58) Field of Classification Search ..... Plt./134
See application file for complete search history.

*Primary Examiner*—Annette H Para

(57) ABSTRACT

A new and distinct variety of rose with long lasting, novel yellow flowers, and attractive foliage with very good disease resistance. It exhibits upright to bushy growth with abundant flowers. The new variety propagates well and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtiglo'.

BACKGROUND OF THE INVENTION

The new variety of rose plant of the present invention origination from a controlled crossing in a breeding program of two distinct parents during the summer of 1997. The crossing was between 'Gold Glow' and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is 'KORtiglo'.

SUMMARY OF THE INVENTION

The new rose plant may be distinguished from its seed parent, 'Gold Glow', by the following combination of characteristics:

1. The flower size of 'KORtiglo' is large, while the flower size of 'Gold Glow' is medium; and
2. the petal count of 'KORtiglo' is very double, while the petal count of 'Gold Glow' is semi-double.

The new rose plant may be distinguished from its pollen parent, an un-named seedling, by the following combination of characteristics:

1. The growth habit of 'KORtiglo' is upright, while the growth habit of the un-named seedling is bushy; and
2. 'KORtiglo' exhibits better disease resistance than the un-named seedling.

The objective of the hybridization was to create a new and distinct rose plant with unique qualities, such as:

1. Uniform growth and flowering;
2. Abundant attractive, recurrent flowers;

3. Attractive and abundant foliage; and
3. Resistance to disease encountered in landscapes and gardens.

This combination of qualities is not present in prior rose cultivars. These objectives have been substantially achieved and in that distinguish 'KORtiglo' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtiglo' was selected in May, 1998 from the seedling beds to be asexually propagated for further evaluation. The first asexual propagation of 'KORtiglo' was done by budding to seedling understocks in July, 1998 at the inventor's nursery in Offenseth-Sparrieshoop, Germany.

This initial and other subsequent propagations conducted in controlled environments demonstrate that 'KORtiglo' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORtiglo'. Specially illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORtilgo', as observed growing in September, 2007 in a nursery in Jackson County, Oreg. on plants of four years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 and issued on Aug. 22, 2006 are compared to 'KORtiglo' in Chart 1.

CHART 1

| Characteristic | 'KORtiglo' | 'KORquelda' |
|---|---|---|
| Open flower diameter | 100-120 mm | 60-70 mm |
| Average petal count | 100-120 | 40 |
| General tonality, open flower | Yellow-Orange Group 20C | Yellow Group 5A |

Parents:

*Seed parent.*—'Gold Glow'.

*Pollen parent.*—An un-named seedling.

Classification:

*Botanical classification.*—*Rosa hybrida,* 'KORtiglo'.

*Commercial classification.*—Hybrid Tea rose.

FLOWER AND FLOWER BUD

*Blooming habit.*—Recurrent.

*Flower bud.*—Size: Upon opening, 30–35 mm in length from base of receptacle to end of bud and 23–26 mm diameter at its widest point. Bud form: Short and globular. Bud color: As sepals first unfold, bud color is Yellow-Green Group 1B with intonations of Red-Purple Group 60B. When ¼ open, the upper surface of petals is Yellow-White Group 158A, and the lower surface is Yellow-White Group 158B. Guard petals: Upper surface is Yellow-Green Group 144B and lower surface is Yellow-Green Group 144B. Intonations of Red-Purple Group 60B on both upper and lower surfaces. Sepals: Size: Average 28–32 mm long×10–12 mm wide. Shape: Sepals generally subulate. Sepal apex is generally cirrose. Weak foliaceous appendages on three of the five sepals. Base is flat at union with receptacle. Quantity: Five. Margins: With many stipitate glands on margins of sepals with foliaceous appendages. Stipitate glands not observed on sepals without appendages. Surface texture: Inner side: Pubescent. Covered in fine white hairs. Outer surface: Smooth. Color: Upper surface: Yellow-Green Group 144A. Lower surface Yellow-Green Group 144A.

*Receptacle.*—Surface: Smooth. Color: Yellow-Green Group 144B. Shape: Funnel shaped. Size: 7–8 mm (h)×10–11 mm (w).

*Peduncle.*—Surface: With stipitate glands. Length: 55–70 mm average length. Diameter: 4–5 mm average diameter. Color: Yellow-Green Group 144B. Strength: Strong. Borne: Multiple flower buds per stem, generally 3 to 5.

Flower bloom:

*Fragrance.*—Light sweet fragrance.

*Duration.*—On the plant 4–6 days. As a cut flower, 5 to 6 days. Senesced petals drop away cleanly.

*Size.*—Large flowered garden rose. When open, the average flower diameter is 100–120 mm and the average flower height is 40 mm.

*Form.*—Quartered rosette. Shape of flower when viewed from the side: Upon opening, upper part: Flat. Upon opening, lower part: Concave. Open flower, upper part: Flattened convex. Open flower, lower part: Concave.

Color:

*Upon opening, petals.*—Outermost petals: Outer Side: Marginal zone: Yellow-Orange Group 19C. Middle zone: Yellow-Orange Group 16C. Inner Side: Marginal zone: Yellow-Orange Group 19C. Middle zone: Yellow-Orange Group 16C. Innermost petals: Outer Side: Yellow-Orange Group 20B. Inner Side: Yellow-Orange Group 16B with intonations of Orange-Red N34D.

*Upon opening, basal petal spots.*—Basal petal spot, outermost petals: Outer Side: Yellow Group 13B. Inner Side: Yellow Group 13A. Basal petal spot, innermost petals: Outer Side: Yellow-Orange Group 13B. Inner Side: Yellow-Orange Group 13A.

*After opening, petals.*—Outermost petals: Outer Side: Orange-White Group 159C. Inner Side: Orange-White Group 159C. Innermost petals: Outer Side: Orange-White Group 159B. Inner Side: Orange-White Group 159B with intonations of Orange-Red Group 35C.

*After opening, basal petal spots.*—Basal petal spot, outermost petals: Outer Side: Yellow Group 9B. Inner Side: Yellow Group 9A. Basal petal spot, innermost petals: Outer Side: Yellow Group 3C. Inner Side: Yellow Group 3B.

General tonality: On open flower Yellow-Orange 20C. No change in the general tonality at the end of the 4th day. Afterwards, general tonality is Yellow-White Group 159C.

Petals:

*Petal count.*—Approximately 100–120 petals under normal conditions.

*Petal reflex.*—Petals reflex slightly.

*Petal edge.*—Width point in center of margin.

*Petal shape.*—Deltoid. Apex shape is pointed. Shape of base is acute.

*Petal size.*—40–50 mm long; 30–35 mm wide.

*Thickness.*—Average.

*Petal arrangement.*—Generally in a regular pattern with overlapping edges.

Petaloids: Present.

*Petaloid count.*—Average of 20–25 per flower.

*Petaloid edge.*—Rough. With undulations on margins.

*Petaloid texture.*—Rough.

*Petaloid shape.*—Obovate. Linear to elliptic.

*Petaloid size.*—Petaloids are 10–15 mm long and 8–12 mm wide.

*Petaloid color.*—Color of inner side Orange-Red Group 32B. Color of outer side is Yellow-Orange Group 15C.

Reproductive organs:

*Pistils.*—Approximately 50–60 present. Stigmas: Location: Slightly inferior in position to anthers. Color: Red-Purple Group 60C. Intonations at apex of Green-Yellow Group 1C. Styles: Covered in fine white hairs. Length: 7–10 mm long. Color: Green-Yellow Group 1C.

*Stamens.*—Approximately 120–140 on average and regularly arranged. Anthers: Size: 3 mm long. Color: Margins: Yellow-Orange Group 22A. Middle: Yellow-orange Group 17D. Pollen: Absent. Filaments: Color: Yellow Group 13B. Length: 3–5 mm.

THE PLANT

*Plant growth.*—Moderate vigor. Upright to bushy habit. When grown as a budded nursery plant the average plant height is 120 cm and the average plant width is 100 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 4–6 per 10 cm of stem. Size: Average length: 4–6 mm. Color: Immature prickles: Greyed-Yellow Group 161B. Mature prickles: Greyed-Yellow Group 161C. Senescing to: Greyed-Orange Group 177B. Shape: Concave. Anthocyanin: Color: Greyed-Red Group 182A observed on apex of immature prickles.

*Leaves and leaflets.*—Normally 3–5 leaflets on normal leaves in middle of the stem. Leaf size: 120–130 mm (l)×90–110 mm (w). Quantity: Average. Texture: Upper side of leaflet: Semi glossy and smooth. Under side of leaflet: Matte and rough. Color, mature foliage: Upper Leaf Surface: Green Group 139A. Lower Leaf Surface: Yellow-Green Group 147A. Color, juvenile foliage: Upper Leaf Surface: Yellow-Green Group 146A. Lower Leaf Surface: Yellow-Green Group 146D. Anthocyanin intonation: Present. Color: Greyed-Purple Group 183A. Location: Intonations present on upper and lower sides of juvenile leaves and margins.

*Stipules.*—Size: 15–20 mm long. 8–9 mm between the tips of the stipule. Main body of stipule 7 mm in width. Shape: Longitudinally flanged. Inverted at base. Winged at apex. Stipule color: Margins: Yellow-Green Group 144A. Middle: Yellow-Green Group 145C. Anthocyanin not observed. Presence of stipitate glands: Present on margins. Margins: Serrated and with stipitate glands.

*Petiole.*—Length: 12–16 mm. Diameter: 2 mm. Petiole color: Yellow-Green Group 145A. Anthocyanin present on juvenile tissue. Color: Greyed-Purple Group 183C. Underneath: A few small prickles underneath. Stipitate glands: Limited numbers of stipitate glands on margins.

*Rachis.*—Length: 21 mm. Diameter: 2 mm. Color: Yellow-Green Group 146A. Anthocyanin present on juvenile tissue. Color: Greyed-Purple Group 183C. Margins: Limited numbers of stipitate glands on margins. Prickles: A few small prickles underneath. Stipitate glands: Limited numbers of stipitate glands on margins.

*Leaflets.*—Size: Average size of the terminal leaflet is 50–60 mm (l)×32–36 mm (w). Shape: Broadly ovate. Base: Ovate. Apex: Acute. Margins: Serrated. Texture: Thick and leathery.

Hips/seed formation: None observed.

Winter hardiness: To date, the variety has been grown successfully in Zone 5.

Disease resistance: Very good resistance to powdery mildew and rust diseases under normal growing conditions.

I claim:

1. A new and distinct variety of rose plant characterized by the following combination of characteristics:

(a) Forms attractive, long lasting yellow flowers;

(b) Exhibits upright to bushy growth habit;

(c) Propagates well using traditional methods, and;

(d) Exhibits very good resistance to disease under normal growing conditions, substantially as herein illustrated and described.

* * * * *

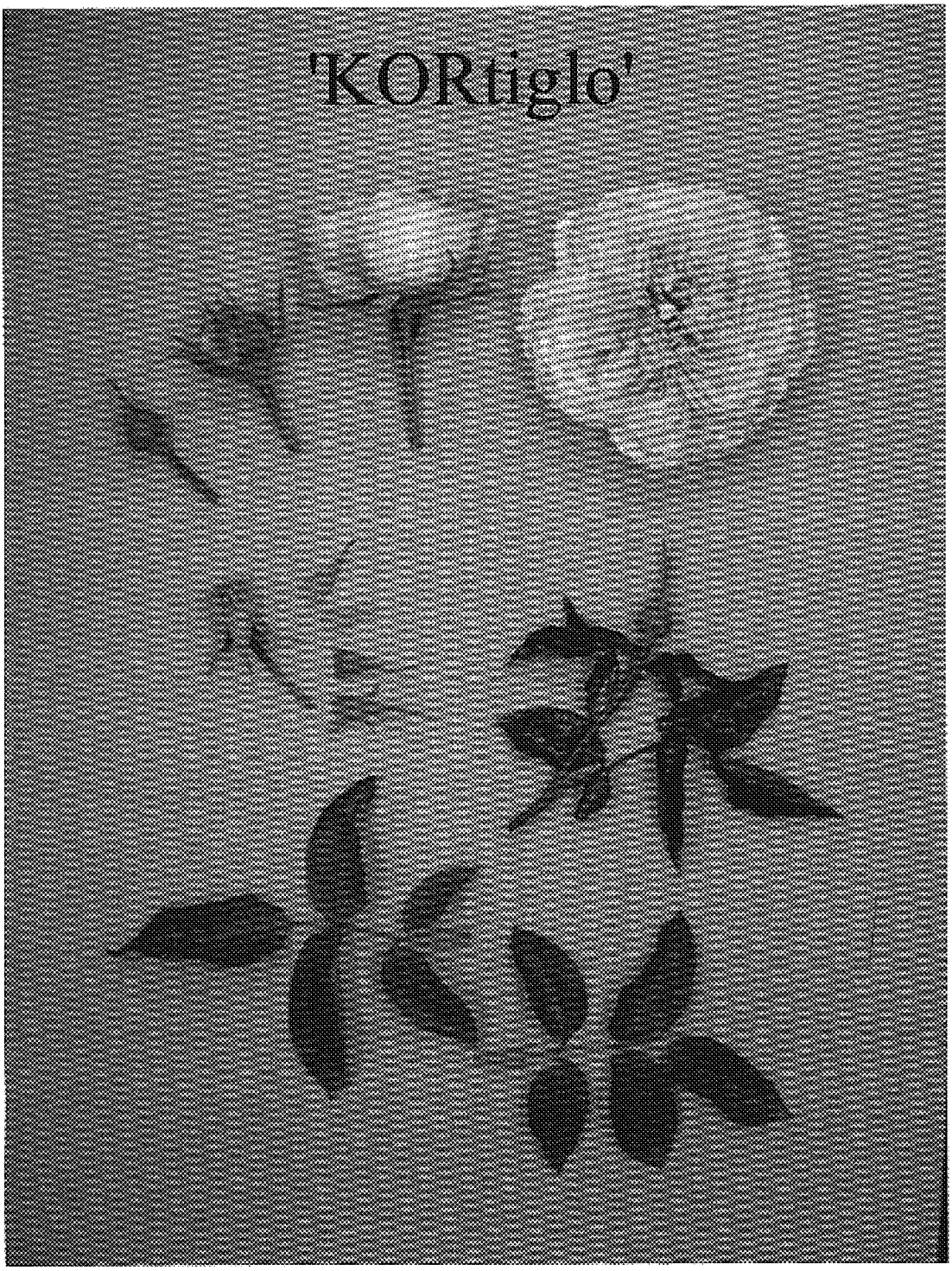
'KORtiglo'